(12) United States Patent
Tang et al.

(10) Patent No.: US 8,452,418 B2
(45) Date of Patent: May 28, 2013

(54) NEURAL PROBE ARRAY AND METHOD OF USE

(75) Inventors: William C. Tang, Irvine, CA (US);
James H. Fallon, Irvine, CA (US);
William E. Bunney, Laguna Beach, CA (US); Ryan Langan, Cypress, CA (US)

(73) Assignee: The Regents of the University of California, Oakland, CA (US)

( * ) Notice: Subject to any disclaimer, the term of this patent is extended or adjusted under 35 U.S.C. 154(b) by 7 days.

(21) Appl. No.: 13/164,599

(22) Filed: Jun. 20, 2011

(65) Prior Publication Data

US 2012/0323102 A1   Dec. 20, 2012

(51) Int. Cl.
*A61N 1/05* (2006.01)
(52) U.S. Cl.
USPC .............................................. 607/118; 607/45
(58) Field of Classification Search
USPC .............................................. 607/45–46, 118
See application file for complete search history.

(56) References Cited

U.S. PATENT DOCUMENTS 5,400,784 A * 3/1995 Durand et al. ................ 600/377
7,991,475 B1    8/2011 Tang et al.
2006/0136024 A1 * 6/2006 Cohen et al. .................. 607/118
2007/0129780 A1 * 6/2007 Whitehurst et al. .......... 607/118
2008/0183258 A1 * 7/2008 Inman ............................ 607/118

OTHER PUBLICATIONS

Branner, Almut et al., Selective Stimulation of Cat Sciatic Nerve Using an Array of Varying-Length Microelectrodes, J. Neurophysiol, 85, 1585-1594, 2001.
Hillman, Todd et al., Cochlear Nerve Stimulation with a 3-Dimensional Penetrating Electrode Array, Otology & Neurotology, Vo. 24, pp. 764-768, 2003.
Normann, Richard A. et al., Microfabricated Electrode Arrays for Restoring Lost Sensory and Motor Functions, Tech. Dig. the 12th International Conference on Solid State Sensors, Actuators, and Microsystems, Boston, MA, Jun. 8-12, 2003, pp. 959-962.

* cited by examiner

*Primary Examiner* — Carl H Layno
*Assistant Examiner* — Paula J Stice
(74) *Attorney, Agent, or Firm* — Vista IP Law Group LLP

(57) ABSTRACT

A neural probe device includes a housing configured to receive a nerve fiber of a subject and an anchor disposed within the housing and configured to fix the nerve fiber relative to the housing. The device further includes a plurality of actuatable, moveable electrodes disposed in the housing along a length of the nerve fiber, each moveable electrode comprising a plurality of projections containing one or more electrodes thereon, wherein actuation of the moveable electrode causes the moveable electrode to move generally transverse to a long axis of the nerve fiber and penetrate the nerve fiber with the plurality of projections. The device is also optionally configured to inject a growth factor into the nerve fiber to maintain the viability of the nerve fiber.

17 Claims, 7 Drawing Sheets

NEURAL PROBE ARRAY AND METHOD OF USE

FIELD OF THE INVENTION

The field of the invention generally relates to methods and devices for the stimulation and/or sensing of electrical signals in nerve fibers.

BACKGROUND OF THE INVENTION

There is a need for neural probe devices that can be used by patients for long periods of time. For example, these devices may be used in amputees or patients suffering from paralysis because of peripheral nerve or spinal cord injury (SCI). Generally, the probe devices may be used to stimulate and/or record electrical signals in nerve fibers. For example, the probe devices may be used as an interface between nervous tissue and various prosthetic devices. As one example, an artificial limb may be designed that interfaces with a neural probe that electrically stimulates one or more sensory neurons within the nerve fibers to give the user the sense of touch. At the same time, the probe devices may contain electrodes that sense the electrical signals in the form of action potentials from motor neurons. These signals could be used to interpret the intentions of the user and translate that into digital signals to control the movements of the artificial limb.

One particular problem with neural probes that has yet to be solved relates to the fact that the neural probes deteriorate over time. These deteriorated probes were either left inside the subject or removed and replaced with a new device. This later approach, however, involves invasive surgical techniques which poses risks and considerable discomfort to the patient. Conventional neural probe devices often have a lifespan of less than one (1) year due to tissue encapsulation, dislocation, probe deterioration, severed nerve regression, and other factors.

There thus is a need for a neural probe that can be used over a longer period of time without having to be replaced. Such a device would advantageously allow both sensing and stimulation of a nerve fiber for a period of time lasting many months or even many years. For example, a device that has a lifespan of decades may never need to be replaced in a patient.

SUMMARY

In one embodiment of the invention, a neural probe device includes a housing configured to receive a nerve fiber of a subject and an anchor disposed within the housing and configured to fix the nerve fiber relative to the housing. The probe device also includes a plurality of actuatable, moveable electrodes disposed in the housing along a length of the nerve fiber, each moveable electrode comprising a plurality of projections containing one or more electrodes thereon, wherein actuation of the moveable electrode causes the moveable electrode to move generally transverse to a long axis of the nerve fiber and penetrate the nerve fiber with the plurality of projections.

In another aspect of the invention, a method of stimulating a nerve fiber includes securing a neural probe device to a nerve fiber, the neural probe device comprising a housing configured to receive a nerve fiber of a subject and including a plurality of moveable electrodes disposed in the housing along a length of the nerve fiber, each moveable electrode comprising a plurality of projections containing one or more electrodes thereon. At least one of the moveable electrodes is actuated to move the at least one moveable electrode generally transverse to a long axis of the nerve fiber and penetrate the nerve fiber with the plurality of projections. An electrical signal is applied to the at least one moveable electrode so as to stimulate the nerve fiber.

In yet another aspect of the invention, a method of interfacing with a nerve fiber includes securing a neural probe device to a nerve fiber, the neural probe device comprising a housing configured to receive a nerve fiber of a subject and including a plurality of moveable electrodes disposed in the housing along a length of the nerve fiber, each moveable electrode comprising a plurality of projections containing one or more electrodes thereon. At least one of the moveable electrodes is actuated to move the at least one moveable electrode generally transverse to a long axis of the nerve fiber and penetrate the nerve fiber with the plurality of projections. An electrical signal in the nerve fiber is detected via the electrodes.

In another aspect of the invention, the same neural probe device that is used to apply electrical signals to the nerve fiber can also be used to detect electrical signals coming from the nerve fiber. That is to say the neural probe device can actively apply or deliver electrical stimulation to the nerve while at the same time can be used to receive electrical response signals.

In still another aspect of the invention, the neural probe device includes an optional reservoir that contains growth factors, drugs or pharmaceuticals. A series of microfluidic channels enables the fluid material retained in the reservoir to be ejected from the neural probe device and into the nerve fiber tissue. The fluid material may be ejected from the electrodes of the neural probe device upon the actuation of moveable stage within the electrodes. An expandable polymer that is actuated via an externally-applied stimulus may be used to actuate and eject the fluid material.

DETAILED DESCRIPTION OF THE ILLUSTRATED EMBODIMENTS

Figure 1:
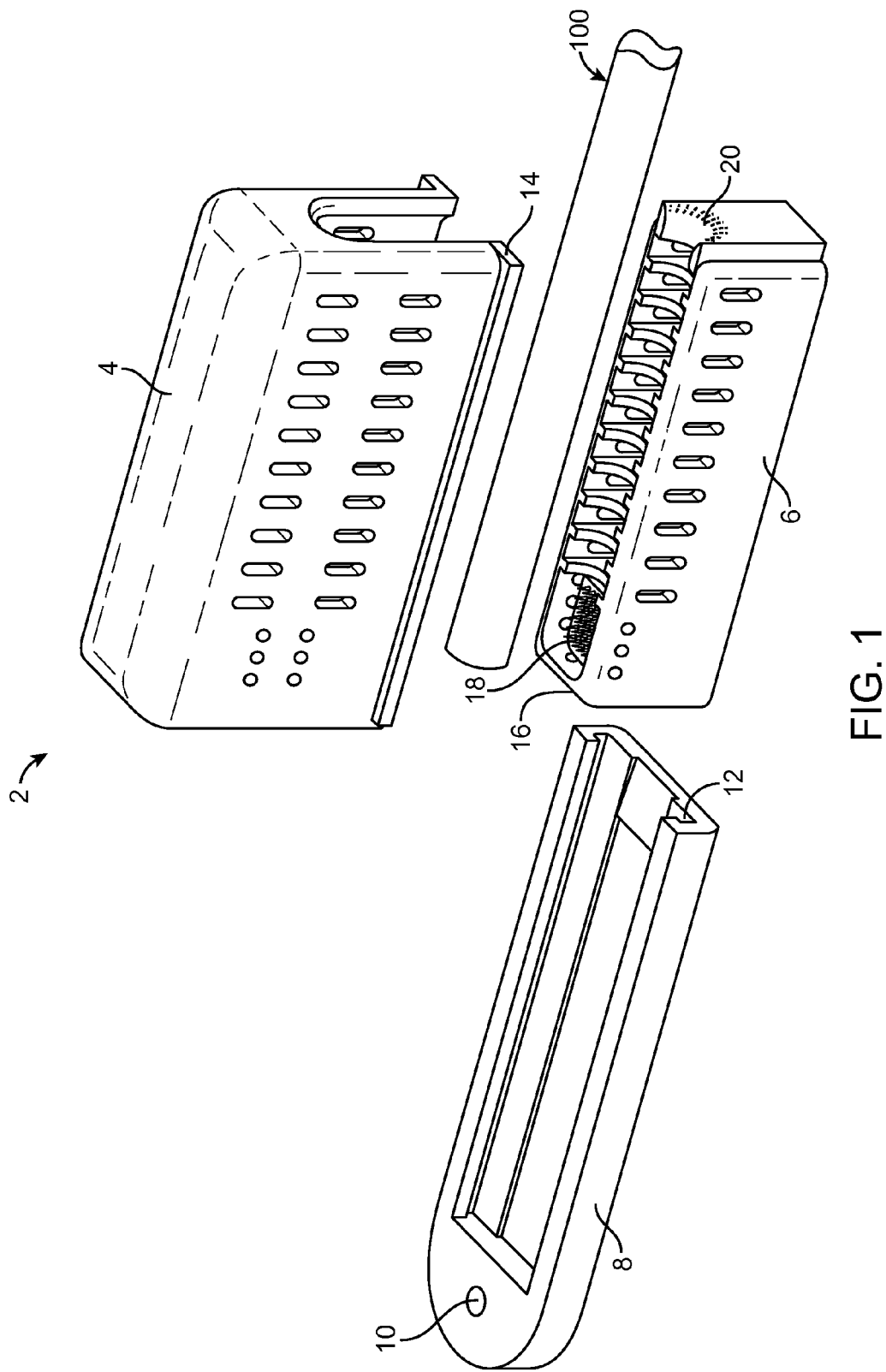
FIG. 1 is an exploded perspective view of a neural probe device according to one aspect of the invention.
Figure 3:
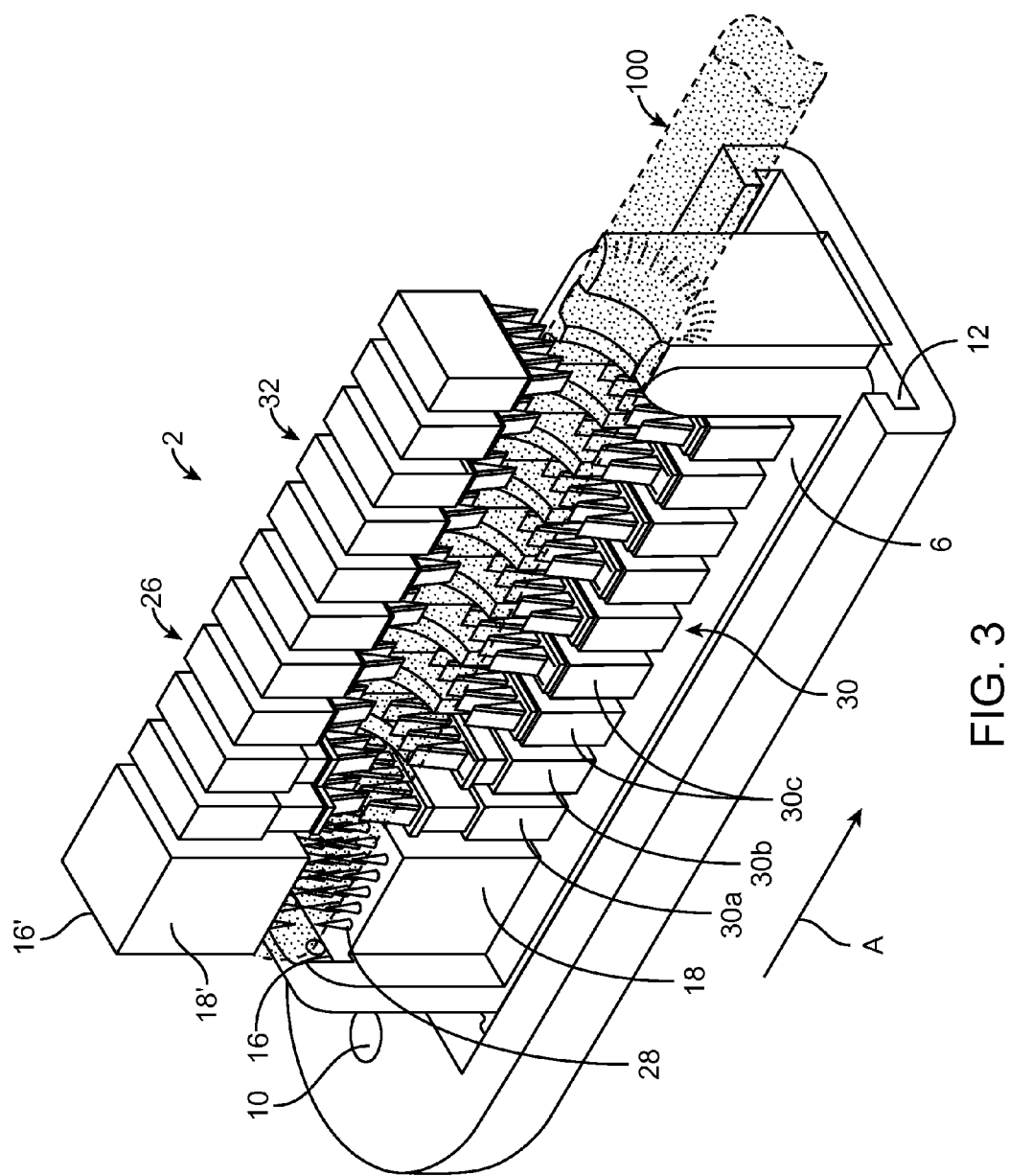
FIG. 3 is a perspective view of a neural probe device with the upper housing removed for clarity.

FIG. 1 illustrates a neural probe device 2 according to one embodiment. The neural probe device 2 includes a housing 4 that is used to at least partially cover a first electrode assembly 6. The neural probe device 2 further includes a mounting plate 8 on which the first electrode assembly 6 is secured to. The mounting plate 8 is used to secure the neural probe device 2 to a bone of the subject in which the neural probe device 2 is implanted. The mounting plate 8 may include one or more apertures 10 for passage of a fastener (not shown) such as, for example, a bone screw or the like. In addition, the housing 4 is configured to interface with the mounting plate 8. In this regard, the mounting plate 8 includes a recess 12 that engages with a flange 14 located on the housing 4 in order that the two may lock together. The housing 4 may lock with the mounting plate 8 using a mechanical lock, a fastener, or even an adhesive (e.g., biocompatible adhesive). The first electrode assembly 6 is affixed or otherwise secured to the mounting plate 8. The first electrode assembly 6 includes at one end, which is referred to as the distal end 16, an anchor 18 that is used to secure a nerve fiber 100 relative to the neural probe device 2. The anchor 18 may include a plurality of projections 28, as seen in FIG. 3, that penetrate the nerve fiber 100 so as to mechanically secure the neural probe device 2 relative to the nerve fiber 100.

Figure 2:
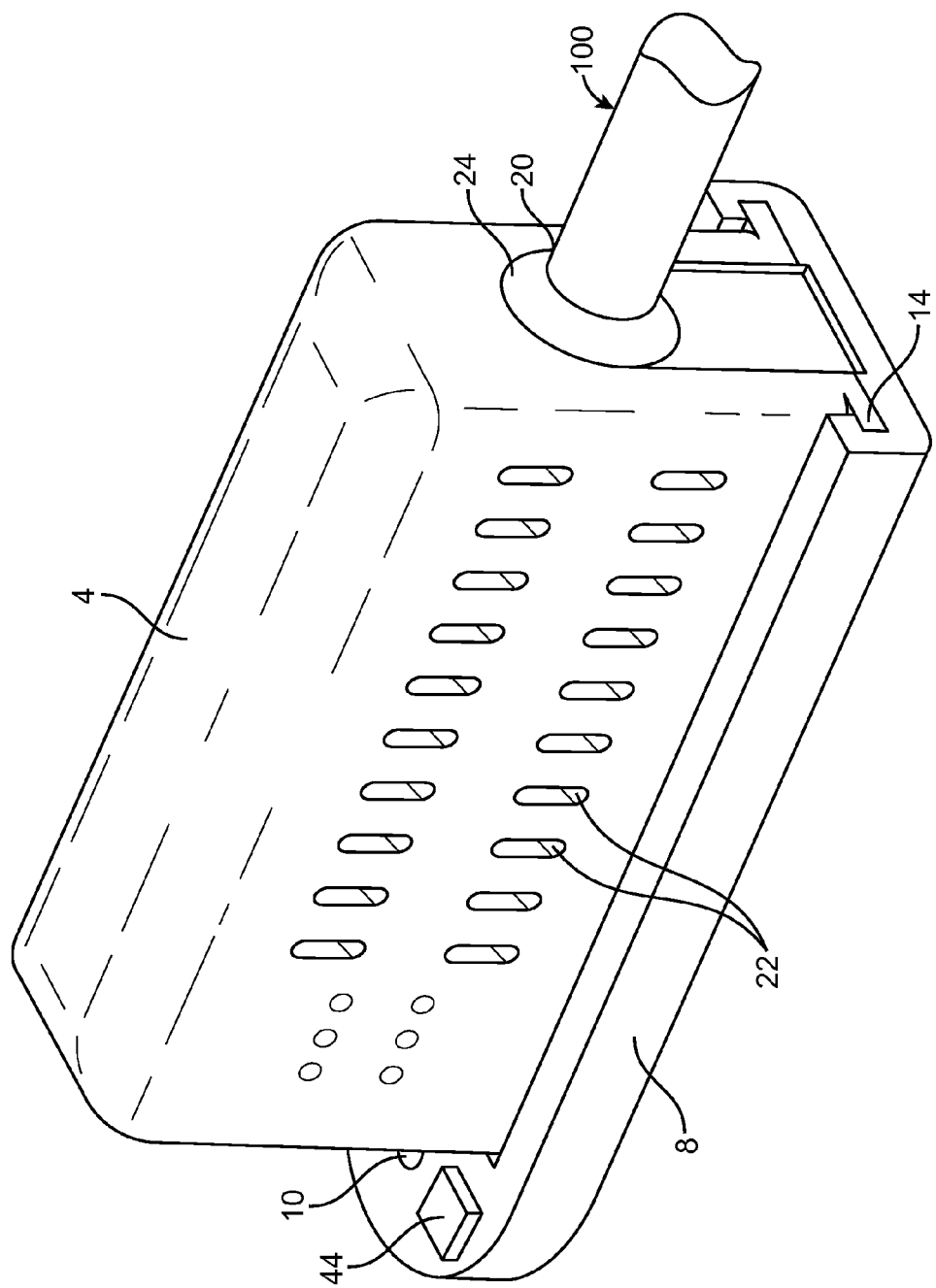
FIG. 2 is a perspective view of the neural probe device in an assembled state.

With reference to FIGS. 1 and 2, an aperture 20 is formed in the housing 4 that is dimensioned for the passage of a nerve fiber 100. The nerve fiber 100 may includes any type of nerve fiber or bundle including, for example, peripheral nerves. FIGS. 1 and 2 illustrate a nerve fiber 100 that is the ascending brachialis nerve but it should be understood that the neural probe device 2 may be used with other types of nerve fibers 100.

FIG. 2 illustrates the neural probe device 2 with the housing 4 in the assembled state. The neural probe device 2 may have any number of dimensions suitable for implantation into a subject. One illustrative dimension is 42 mm×15 mm×24 mm although other dimensions are contemplated to fall within the scope of the invention. The housing 4 may include one or more optional fluid ports 22 that allow fluid to flow into and out of the device 4. The ports 22 may be dimensioned to receive the ingrowth of blood vessels and migrating cells which provide additional nutritional and metabolic support to the enclosed nerve fiber 100, as well as migrating cells from tissues surrounding the neural probe device 2 which reduce the formation of scar tissue within the enclosed nerve fiber 100, and encourage the migration of progenitor cells which aid in the viability and normal physiology of the enclosed nerve fiber 100.

The housing 2 may be made from a biocompatible material such as, for instance, biocompatible titanium. At the interface between the nerve fiber 100 and the aperture 20 in the housing 4, a bioadhesive 24 may be placed around the nerve fiber 100. The bioadhesive 24 adheres to the filleted edge of the aperture 20.

FIG. 3 illustrates a perspective view of the interior portion of the neural probe device 2 with the housing 4 removed for clarity purposes. In the embodiment of FIG. 3, the neural probe device 2 includes the first electrode assembly 6 as well as a second electrode assembly 26. The second electrode assembly 26 is disposed on an opposing side of the nerve fiber 100 and, as explained herein, is used to hold individual moveable electrodes that are actuated to mechanically interface with the nerve fiber 100. The device 2 includes an anchor 18 located at the distal end 16 of the first electrode assembly 6. Optionally, the second electrode assembly 26 may include an anchor 18' at its distal end 16' in which the nerve fiber 100 is sandwiched between the two anchor portions 18, 18'.

The anchor(s) 18, 18' may include a number of needle-like projections 28 that physically contact the nerve fiber 100 to fixedly secure the same within the neural probe device 2. As seen in FIG. 3, the first electrode assembly 6 includes a plurality of actuatable, moveable electrodes 30 disposed along the length of the nerve fiber 100. In a similar manner, the second electrode assembly 26 also includes a plurality of actuatable, moveable electrodes 32 disposed along the length of the nerve fiber 100. Each actuatable, moveable electrode 30, 32 may be independently actuated. Actuation is meant to indicate that the moveable electrode 30, 32 moves some distance generally perpendicular to the long axis of the nerve fiber 100. Actuation includes partial as well as full extension of the moveable electrodes 30, 32 as explained below.

Figure 4:
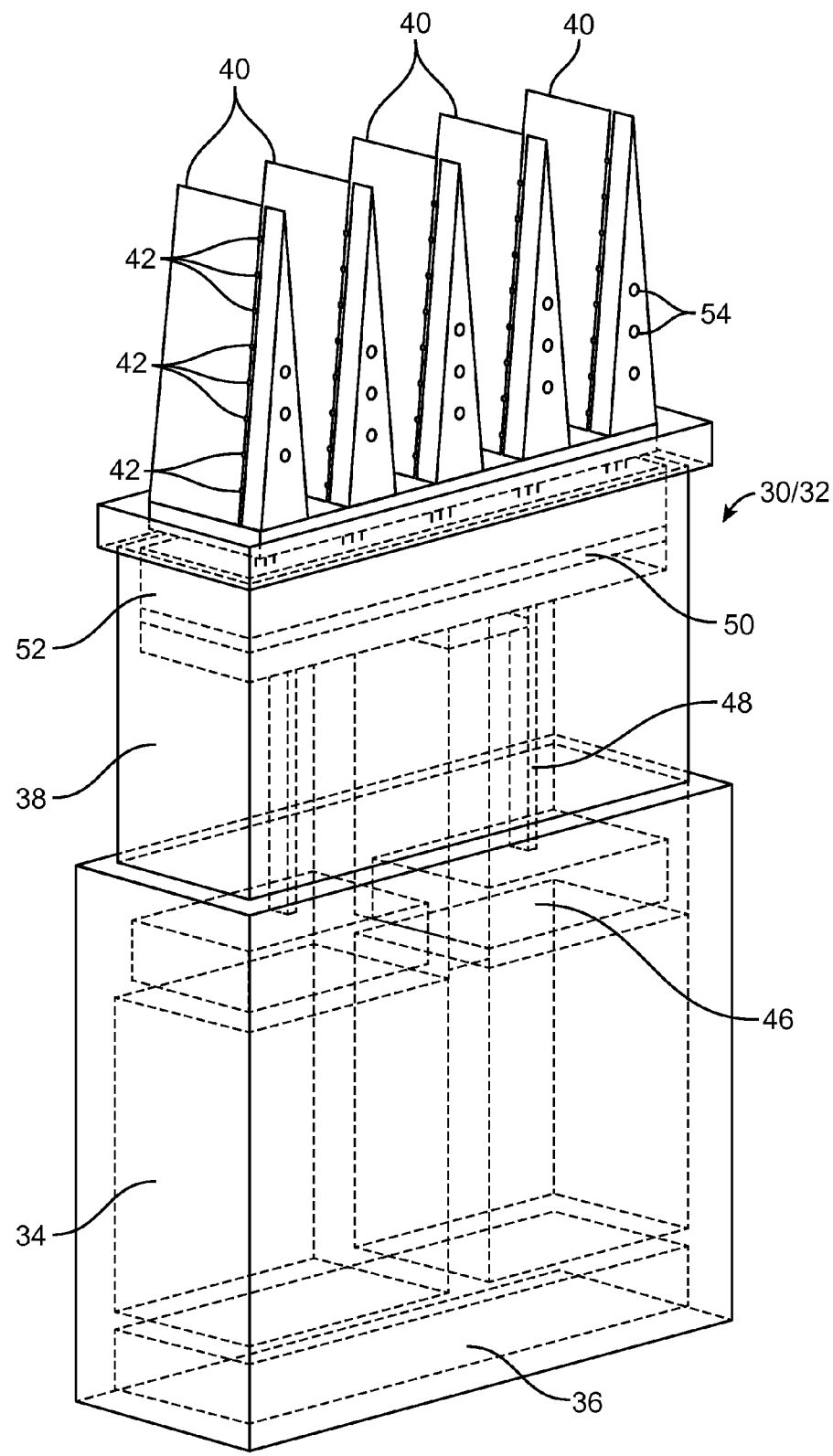
FIG. 4 is a perspective view of a single moveable electrode according to one embodiment of the invention.
Figure 6:
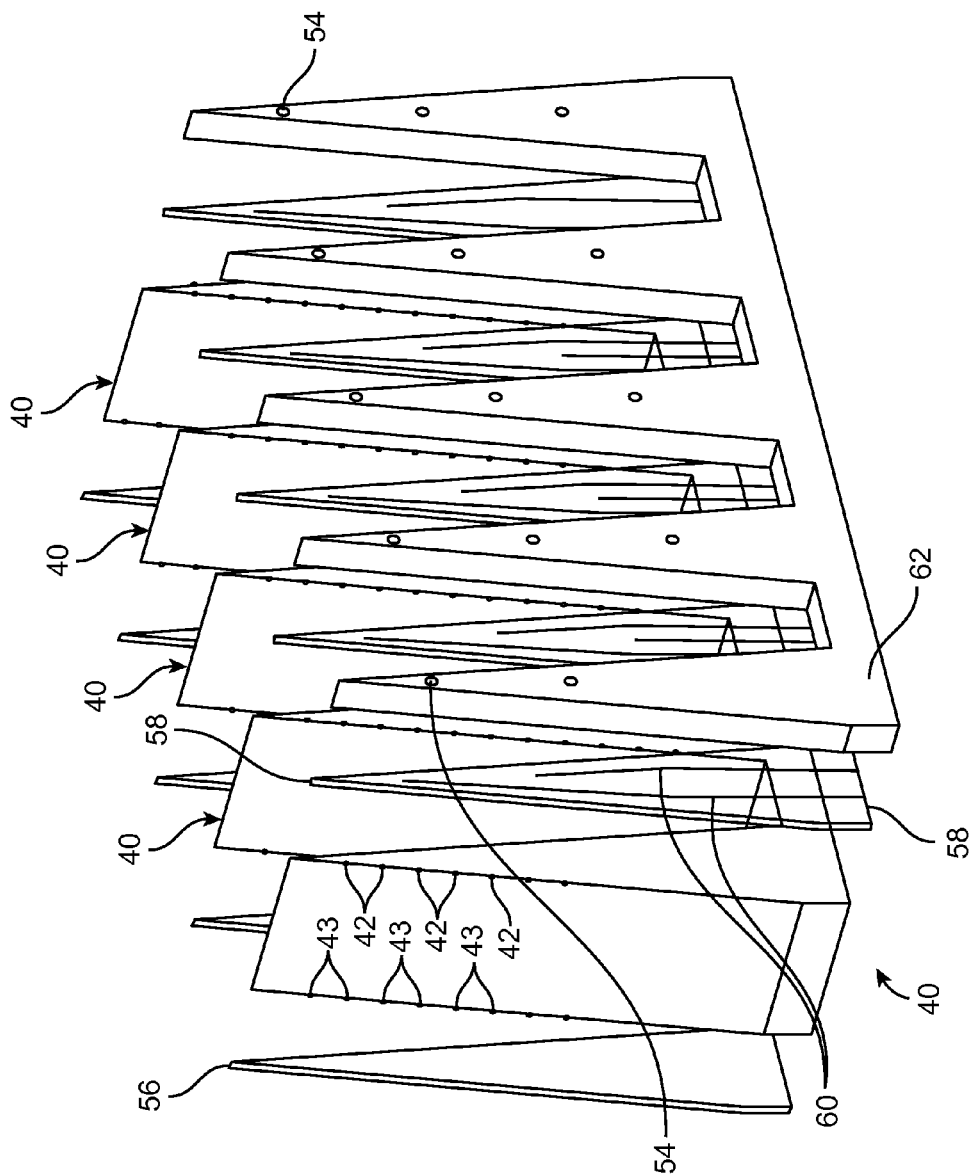
FIG. 6 is a perspective view of the construction of the layers used in the moveable electrode according to one embodiment of the invention.

In one embodiment, as best seen in FIG. 4, the moveable electrodes (30 or 32) include a base 34 which may be in the form of a cylinder that includes an a first expandable stage 36 therein that is interposed between the base 34 and a piston element 38. The first expandable stage 36 may include an expanding polymer that expands in response to an externally applied stimulus. The externally applied stimulus may include heat or electricity. For example, the expanding polymer may include an electroactive polymer. For example, electroactive polymers such as polypyrole may be used which exhibits significant volumetric expansion when exposed to electric fields in an ionic fluid. Of course, other polymers or expanding materials may also be used as speed is not required. Upon application of stimulus signal, the first expandable stage 36 undergoes dimensional expansion to thereby move the piston element 38 relative to the base 34. Located at one of the piston element is a plurality of projections 40. These projections 40 are dimensioned and configured to penetrate the nerve fiber 100. Each projection 40 contains a plurality of electrodes 42 disposed along the projection surface. The electrodes 42 may be used to pick-up or receive electrical signals from the nerve tissue 100 or, alternatively, the electrodes 42 may be used to actively deliver electrical signals to the nerve tissue 100. In one embodiment, on set of electrodes 42 may be used to deliver electrical signals while a different set of electrodes 43 may be used to receive electrical signals. Such an embodiment is illustrated in FIG. 6. In still another embodiment, the electrodes 42 may be used to both deliver and receive electrical signals. The electrodes 42 are connected either through wires or other electrical pathways to a control unit 44 (illustrated in FIG. 2) that, in some embodiments, is integrated into the neural probe device 2. The control unit 44 may contain a microprocessor or the like along with instructions therein for the delivery and/or receipt of electrical signals to the nerve tissue 100. The control unit 44 may be powered through an internal battery or other power source. Alternatively, the control unit 44 may be powered externally via inductive coupling. In still another alternative, the control unit 44 may be connected through a wire harness or the like that passes percutaneously to an externally located connector that can then be coupled to a separate source of power that is used or even worn by the subject. Similarly, data transfer to and from the neural probe device 2 may occur through wireless transmissions to and from the control unit 44.

During operation of the neural probe device 2, individual moveable electrode 30, 32 are actuated to engage (i.e., penetrate) with the nerve fiber 100. In one aspect, the moveable electrodes 30, 32 are actuated via a piston-like mechanism that is triggered via an externally applied control signal (e.g., wireless signal). An expanding polymer (as explained below) may be used to actually move or actuate the electrodes 30, 32. In one embodiment, the particular moveable electrodes 30, 32 are not actuated into position until the point of use. For example, FIG. 3 illustrates a fully actuated electrode 30a located adjacent to the anchor 18. Next to the fully actuated electrode 30a is a "half-actuated" electrode 30b. The remaining electrodes 30c are non-actuated or recessed within their respective bases 34. In one preferred aspect of the invention, individual electrodes 30, 32 are able to be selectively actuated. Such selective actuation may include, for example, the actuation of the electrodes 30, 32 toward the distal end 16 first followed by actuation of the move proximally located electrodes 30, 32 (those in the direction of arrow A). For example, software stored on the control unit 44 may be pre-programmed or given control signals to selectively actuate electrodes 30, 32 starting from the distal end 16 and progressively actuating the proximally adjacent electrodes 30, 32.

The neurological signals sensed by the neural probe device 2 will typically deteriorate over time due to a number of factors. Once the particular movable electrode 30, 32 stops functioning or the sensing and/or stimulating functions drop below a minimum threshold, a problem that plagues all senor arrays, the next adjacent electrode 30, 32 is actuated and takes over operation from the deteriorated or failed electrode 30, 32. Generally, this actuation takes place in the order as illustrated in FIG. 3, namely, those electrodes 30, 32 located closest to the anchor 18 (near distal end 16/16') are used first and adjacent electrodes 30, 32 located further from the anchor 18 are then selectively actuated. As the signal fade pattern travels up the nerve fiber 100 proximally (towards the CNS, brain), the electrodes 30, 32 sequentially replace the deteriorated one to follow it. By having multiple electrodes 30, 32 located along the length of the nerve fiber 100, the lifespan of the neural probe device 2 is prolonged drastically.

With reference to FIG. 4, in still another aspect of the invention, each moveable electrode 30, 32 is configured to further extend the life of the neural probe device 2 by the injection of natural growth factors, drugs or pharmaceuticals to the nerve fiber 100. In one embodiment, each moveable electrode 30, 32 has the ability to inject or otherwise release drugs into the nerve fiber 100 upon actuation. In one aspect, the drug is a growth factor that is injected into the nerve fiber 100. The injected growth factor keeps the nerve fiber 100 viable, suppressing or restricting the signal pathway that triggers the immunological responses. Examples of growth factor include, but are not limited to, TGF alpha, BDNF, FGF2, FGF1,4,8,10, bFGF, NGF, VEGF, NT3, NT4, EGF, retinoic acid and derivatives, EPO, PDGF, GM-CSF, G-CSF, TGF beta, BMP, and TNF.

FIG. 4 illustrates a single moveable electrode 30 that includes in addition to the first expandable stage 36 a second expandable stage 46. The second expandable stage 46 may be located within the piston element 38 of the first expandable stage 36. As seen in FIG. 4, the second expandable stage 46 interfaces within its own piston element 48. The piston element 48 terminates in a plate 50 that is used to compress a reservoir 52 that contains natural growth factors, drugs or pharmaceuticals. The second expandable stage 46 may include an expanding polymer that expands in response to an externally applied stimulus. The externally applied stimulus may include heat or electricity. For example, the expanding polymer may include an electroactive polymer. Upon application of stimulus signal, the second expandable stage 46 undergoes dimensional expansion to thereby move the piston element 48 which presses the plate 50 against the reservoir 52.

FIG. 4 illustrates a reservoir 52 located with growth factor that is to be injected into the nerve fiber 100. Upon actuation of the second expandable stage 46, the growth factor is hydraulically ejected out of ports 54 located on each projection 46 of the electrode 30, 32. Expansion of the polymer, which may also be an electroactive polymer, forces the growth factor (in liquid form) out the ports 54 and into the nerve fiber 100. In this aspect, the moveable electrodes 30, 32 has a first expansion stage 36 to insert the projections 40 into the nerve fiber 100 and a second expansion stage 46 to eject the growth factor or other medical compounds into the surrounding nerve fiber 100.

Another aspect of the invention is that the moveable electrode arrays 30, 32 on opposing sides of the nerve fiber 100 are used. This approach allows more electrode 42 point accesses with a smaller proportion of the nerve tissue being displaced. In addition, the symmetrical penetration of the nerve fiber 100 significantly enhances the mechanical stability of the implants in nerve tissue and thus decreases the functional deterioration due to implant dislocation which is common in prior probe designs. Further, the moveable electrode arrays 30, 32 provide additional mechanical stability, preventing the nerve fiber 100 from being pushed off by any scar tissue. Additional mechanical stability is provided by the anchor 18 located at the end of the nerve fiber 100.

Figure 5:
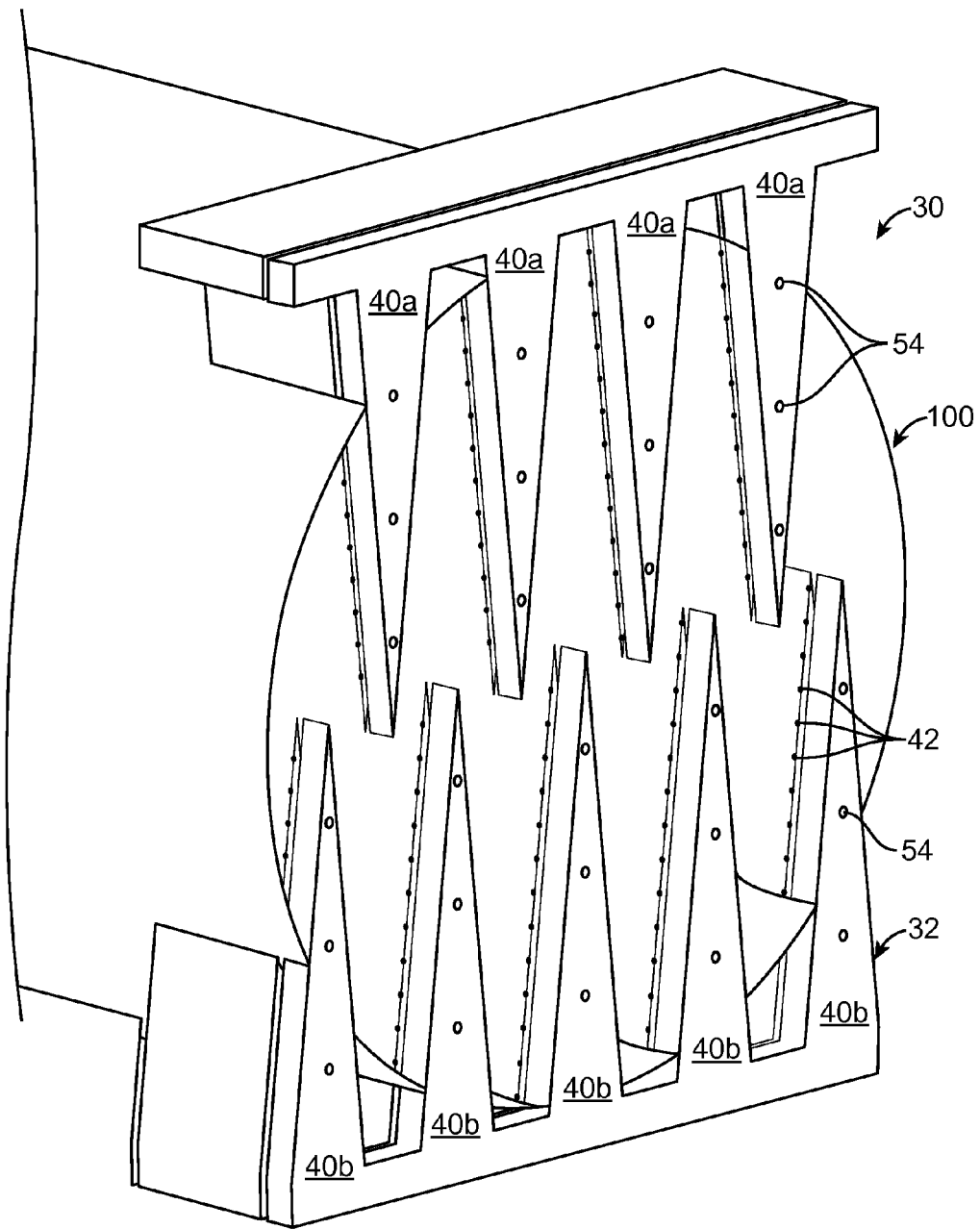
FIG. 5 is a perspective, cross-sectional view of opposing moveable electrode being positioned within a nerve fiber.

FIG. 5 illustrates the projections 40a, 40b of opposing electrodes 30, 32 that are inserted into the nerve fiber 100. As seen in FIG. 5, the projections 40a, 40b of each electrode 30, 32 are staggered to maximize the number of electrodes 42 in a given section of nerve tissue. The functional lifespan of the nerve fiber 100 is extended by minimizing the mechanical trauma to the nerve tissue by having electrodes 42 being inserted on either side of the nerve fiber 100. In this regard, more electrodes 42 can be placed in a shorter length of the nerve fiber 100, saving more the nerve tissue. For example, more than 250 separate electrodes 42 may be positioned in a 1.5 mm length of nerve fiber 100. In the example seen in FIG. 5, there are nine (9) projections 40 per opposing set of arrays 30, 32 with dozens of electrodes 42 on each projection 40. Of course, higher densities are possible with improved fabrication processes.

FIG. 6 illustrates a layered structure used for the projections 40 of the moveable electrodes 30, 32. In this structure, glass layers 56, 58 are formed on either side the main, silicon-based projection 40. The glass layers 56, 58 serve to insulate the electrode leads. In addition, one glass layer 58 has etched channels 60 or conduits formed therein that permit passage of the drug or pharmaceutical (e.g., growth factor) from the reservoir 52 into the nerve fiber 100. A layer of biocompatible silicon 62 may be used to seal the channels 60 as shown in FIG. 6.

Figure 7:
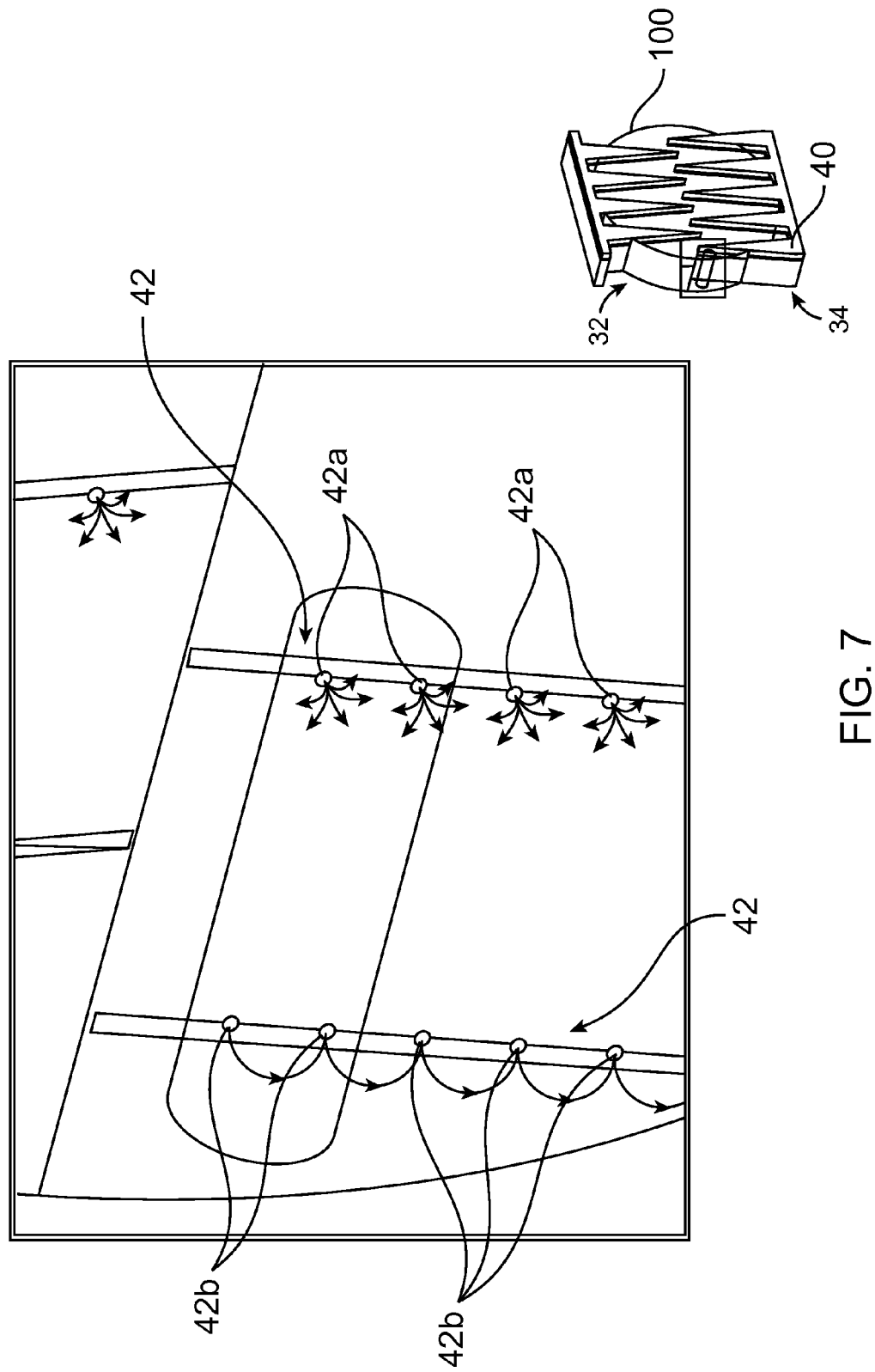
FIG. 7 illustrates both monopolar and bipolar electrical fields generated at the electrodes located on a single projection of a moveable electrode.

FIG. 7 illustrates a magnified view of the surface of a projection 40 containing electrodes 42. Electrodes 42a (on the right hand side) on the projection 40 are shown operating in a monopolar mode. Electrodes 42b (on the left hand side) of the projection 40 in FIG. 7 are illustrated as operating in bipolar mode. The electrodes 42 may be formed from gold or other electrically conductive and biocompatible material (e.g., iridium oxide) and a second, return or ground electrode (not shown) may be located elsewhere on the neural probe device 2.

The electrodes 42a described above on the leading face of the projection 40 may be used to stimulate the nerve fiber 100. These electrodes 42a may be made from gold. Electrical signals may be provided via the control unit 44, an external computer, a circuit, or a prosthetic device. The trailing face of the projection 40 may include the iridium oxide electrodes 42b which may be used to measure the electrical properties of the nerve fiber 100. The output may be directed to a low noise, high gain amplifier (as part of or separate from control unit 44) which can then send signals remotely to a receiver or other device located external to the patient. The entire input/output and control functions may be contained in circuitry disposed inside the housing 4. The circuitry may be powered externally, for example, by inductive coupling and thus there is no need to replace batteries in the neural probe device 2. Of course, other methods of powering the neural probe device 2 may also be employed and still fall within the scope of the invention.

The first and second electrode assemblies 6, 26 may be fabricated with Micro-Electro-Mechanical Systems (MEMS) technology. Both surface and bulk micromachining can be used to fashion the final design of the first and second electrode assemblies 6, 26. For example, the base 34, piston elements 38, 48 along with the drug reservoir 52 can be created with a combination of MEMS and precision laser machining.

The neural probe device 2 described herein may interface with a prosthetic limb (not shown) with robotic functionality. For example, the neural probe device 2 may be used to receive electrical signals from motor neurons contained within a nerve fiber 100. The electrical signals may then be analyzed and/or processed through the control unit 44 which in turn may control the prosthetic limb. For example, the neural probe device 2 may receive electrical signals from motor neurons that would indicate that the subject with the implanted neural probe device 2 is attempting to grip an object. The control unit 44 or another separate control unit (not shown) may process this data and, in turn, issue control signals to a robotically-controlled prosthetic limb to move the fingers and thumb together in a gripping motion. While the example described herein is done in the context of gripping motion it should be understood that the particular electrical signal from the motor neurons can be used in a similar manner for other movements and other robotically-controlled prosthetic devices.

While embodiments of the present invention have been shown and described, various modifications may be made without departing from the scope of the present invention. The invention, therefore, should not be limited, except to the following claims, and their equivalents.

What is claimed is:

1. A neural probe device comprising:
a housing configured to receive a nerve fiber of a subject;
an anchor disposed within the housing and configured to fix the nerve fiber relative to the housing; and
a plurality of actuatable, moveable electrodes disposed in the housing along a length of the nerve fiber, each moveable electrode comprising a base containing an electroactive polymer and a piston element having a plurality of projections containing one or more electrodes thereon, wherein actuation of the moveable electrode causes volumetric expansion of the electroactive polymer and moves the piston element generally transverse to a long axis of the nerve fiber and penetrates the nerve fiber with the plurality of projections.

2. The device of claim 1, wherein the moveable electrode comprises a reservoir configured to hold a growth factor and an electroactive polymer based actuator configured to eject the growth factor via an exit port, the reservoir being coupled to the exit port in the moveable electrode.

3. The device of claim 2, wherein the growth factor comprises one or more of TGF alpha, BDNF, FGF2, FGF1,4,8,10, bFGF, NGF, VEGF, NT3, NT4, EGF, retinoic acid and derivatives, EPO, PDGF, GM-CSF, G-CSF, TGF beta, BMP, and TNF.

4. The device of claim 2, wherein the actuator comprises an electroactive polymer configured to eject the growth factor.

5. The device of claim 2, wherein the plurality of moveable electrodes disposed in the housing comprise a first plurality of moveable electrodes disposed on a first side of the housing and a second plurality of moveable electrodes disposed on a second, opposing side of the housing.

6. The device of claim 5, further comprising a control unit having a microprocessor, the microprocessor operatively coupled to the plurality of actuable, moveable electrodes via electrical pathways, the control unit configured to selectively actuate pairs of moveable electrodes from the first and second plurality of moveable electrodes.

7. The device of claim 1, wherein the at least one electrode comprises monopolar electrodes.

8. The device of claim 1, wherein the at least one electrode comprise bipolar electrodes.

9. The device of claim 1, wherein the anchor comprises a plurality of projections configured to penetrate the nerve fiber.

10. A method of stimulating a nerve fiber comprising:
securing a neural probe device to a nerve fiber, the neural probe device comprising a housing configured to receive a nerve fiber of a subject and including a plurality of moveable electrodes disposed in the housing along a length of the nerve fiber, each moveable electrode comprising a base containing an electroactive polymer and a piston element having a plurality of projections containing one or more electrodes thereon,
actuating the electroactive polymer of the at least one of the moveable electrodes to move the at least one moveable electrode generally transverse to a long axis of the nerve fiber and penetrate the nerve fiber with the plurality of projections; and
applying an electrical signal to the at least one moveable electrode so as to stimulate the nerve fiber.

11. The method of claim 10, further comprising releasing a growth factor into the nerve fiber via the neural probe.

12. The method of claim 10, wherein actuating comprising actuating a first pair of opposing moveable electrodes so as to pinch the nerve fiber from opposing sides.

13. The method of claim 12, further comprising actuating a second pair of opposing moveable electrodes so as to pinch the nerve fiber from opposing sides, wherein said second pair of opposing moveable electrodes are located proximal relative to the first pair of opposing moveable electrodes.

14. A method of interfacing with a nerve fiber comprising:
securing a neural probe device to a nerve fiber, the neural probe device comprising a housing configured to receive a nerve fiber of a subject and including a plurality of moveable electrodes disposed in the housing along a length of the nerve fiber, each moveable electrode comprising a base containing an electroactive polymer and a piston element having a plurality of projections containing one or more electrodes thereon,
actuating the electroactive polymer of the at least one of the moveable electrodes to move the at least one moveable electrode generally transverse to a long axis of the nerve fiber and penetrate the nerve fiber with the plurality of projections; and
detecting an electrical signal in the nerve fiber via the electrodes.

15. The method of claim 14, further comprising releasing a growth factor into the nerve fiber via the neural probe.

16. The method of claim 14, wherein actuating comprising actuating a first pair of opposing moveable electrodes so as to pinch the nerve fiber from opposing sides.

17. The method of claim 16, further comprising actuating a second pair of opposing moveable electrodes so as to pinch the nerve fiber from opposing sides, wherein said second pair of opposing moveable electrodes are located proximal relative to the first pair of opposing moveable electrodes.

* * * * *